United States Patent
Krajewski et al.

(10) Patent No.: US 8,357,250 B2
(45) Date of Patent: Jan. 22, 2013

(54) RECOVERY HEAT TREATMENT TO IMPROVE FORMABILITY OF MAGNESIUM ALLOYS

(75) Inventors: Paul E. Krajewski, Troy, MI (US); Ravi Verma, Shelby Township, MI (US); Jon T. Carter, Farmington, MI (US); Joshua D. Lasceski, Harrison Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 1124 days.

(21) Appl. No.: 12/181,618

(22) Filed: Jul. 29, 2008

(65) Prior Publication Data

US 2010/0024924 A1 Feb. 4, 2010

(51) Int. Cl.
*C21D 11/00* (2006.01)
(52) U.S. Cl. ......................... 148/508; 148/667
(58) Field of Classification Search .................. 148/508, 148/666, 667
See application file for complete search history.

(56) References Cited

U.S. PATENT DOCUMENTS

| | | | |
|---|---|---|---|
| 2,314,853 A | 3/1943 | Brandt et al. | |
| 2,520,753 A | 8/1950 | Ball et al. | |
| 4,323,399 A | 4/1982 | Dubost et al. | |
| 5,316,598 A | 5/1994 | Change et al. | |
| 6,511,560 B2 | 1/2003 | Seki et al. | |
| 2005/0067068 A1 | 3/2005 | Shimizu et al. | |
| 2006/0231173 A1 | 10/2006 | Liang et al. | |
| 2007/0079913 A1 * | 4/2007 | Krajewski | 148/667 |

FOREIGN PATENT DOCUMENTS

| | | |
|---|---|---|
| DE | 10003970 | 8/2001 |
| DE | 102004035043 | 4/2006 |
| WO | 2008044936 | 4/2008 |

* cited by examiner

*Primary Examiner* — Scott Kastler
(74) *Attorney, Agent, or Firm* — BrooksGroup

(57) ABSTRACT

The formability of coiled and annealed (O-temper) magnesium alloy sheet material in high temperature forming operations is sometimes adversely affected by small amounts of cold work introduced into the fine grained material during handling of the coil and unwinding it to obtain blank workpieces for hot stamping, hot blow forming, or the like. When necessary, the formability of the sheet material with regions of hard worked microstructure may be improved by predetermining a recovery heat treatment using small portions of the material in formability tests. The recovery heat treatment, determined for the specific coiled stock, may then be applied to the material of the coil as it is used in making vehicle body panels or the like.

12 Claims, 1 Drawing Sheet

Heat Treatment Before Bulge Test

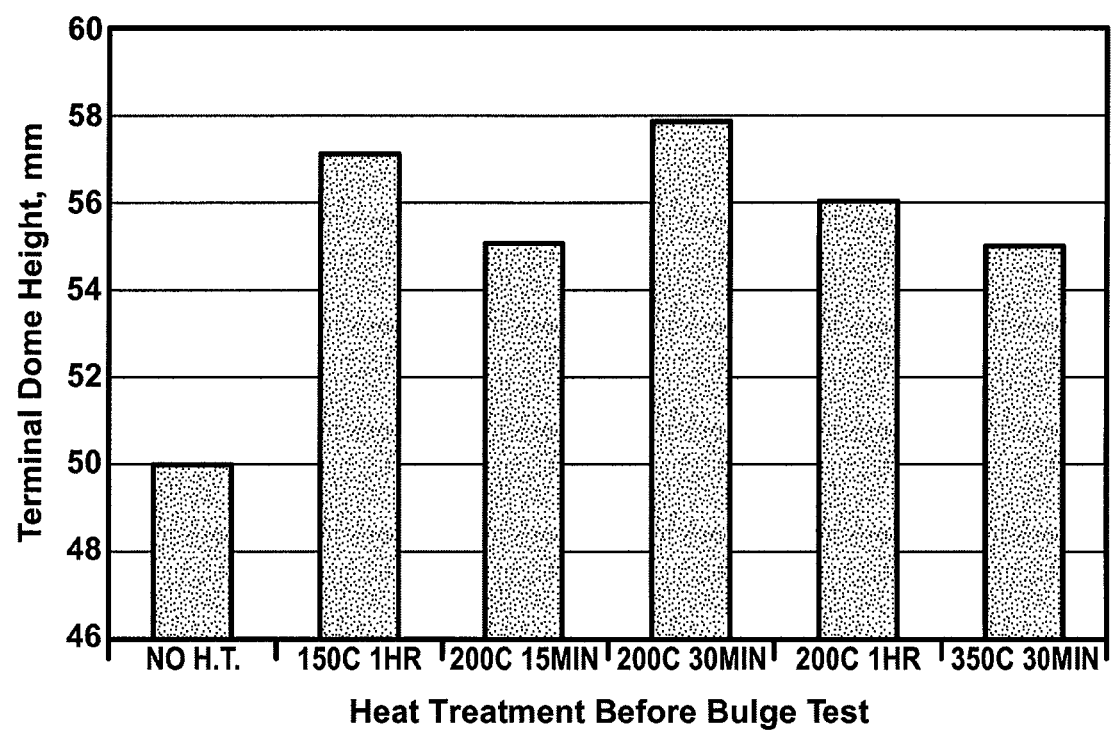

RECOVERY HEAT TREATMENT TO IMPROVE FORMABILITY OF MAGNESIUM ALLOYS

TECHNICAL FIELD

This invention pertains to hot forming of magnesium alloy sheet blanks from a starting material that has been rolled to a desired sheet thickness, coiled, and annealed to an O-temper condition. More specifically, this invention pertains to a heat treatment for sheet metal blanks prepared from the coiled and annealed stock to improve formability of the magnesium alloy blanks in hot stamping or hot blow forming processes to produce sheet metal parts such as automotive vehicle body panels.

BACKGROUND OF THE INVENTION

There is interest in forming relatively light-weight magnesium alloy sheet materials into, for example, automotive vehicle body panels. Such panels may be formed from initially flat, sheet metal blanks having nominal dimensions of, e.g., about 1000 mm×1500 mm×1-3 mm. So far, automotive manufacturing engineers have had more experience in forming body panels from aluminum sheet alloys, although magnesium alloys are hot formable at about the same temperature ranges as aluminum alloys and offer further reductions in weight.

At the present time the forming of magnesium alloy sheet metal body panels requires forming the sheet metal at elevated forming temperatures. The specific hot forming practice used depends largely on the complexity of the shape of the panel product; i.e., the severity of the deformation required to be introduced into a magnesium alloy sheet metal blank. Some panel shapes, like engine compartment hoods, may be formed by hot stamping magnesium alloy sheet blanks between facing, complementary heated forming dies without preheating the workpieces. Other, more complex panel shapes may require that the workpieces be preheated for hot blow forming. Magnesium alloy vehicle lift gates and door panels often require hot blow forming temperatures and practices to deform the sheet material into a functional and streamlined panel shape.

Hot blow forming of magnesium sheet metal typically involves heating of a sheet metal blank to approximately 450° C. in a preheat furnace, robotically transferring that sheet to a position between facing dies which are also heated to approximately that same temperature, clamping the periphery of the sheet blank shape between die halves to establish a gas-tight seal, and then applying gas pressure to one side of the heated sheet to blow it into a facing die cavity and against a forming surface to form the desired shape. Then the gas pressure is released, the die is opened, and the formed panel is removed and allowed to cool. Alternatively, in some cases, instead of using a preheat furnace, the sheet may be heated by the hot die before or during forming. In either case, the sheet is typically heated to approximately 450° C., and then held at that temperature for a short time to assure a suitably uniform temperature prior to application of the forming pressure.

In forming by hot stamping, the magnesium alloy sheet material is usually preheated to a temperature below about 350° C. and stamped between heated, complementary forming dies carried on opposing press platens and maintained at a specified forming temperature. Upon press closure, the heated sheet is contacted by at least one die surface which rams and stretches the sheet against a facing surface. As in hot blow forming, the sheet workpiece and the hot stamping tools are at a specified hot stamping temperature before deformation of the workpiece begins.

These hot forming practices are well developed for aluminum sheet alloys and the fully preheated workpieces are formed readily into body panels of complex shape. But the application of such hot forming practices to magnesium sheet alloys has generally been slower and more easily applied to the forming of articles with lower shape complexity.

SUMMARY OF THE INVENTION

This invention has been made for elevated temperature forming of magnesium sheet metal alloys. The sheet metal alloys are typically about one to three or four millimeters in thickness. In automotive vehicle body panels, for example, a sheet metal blank is formed into an inner or outer (or both) body panel such as a door panel, a lift gate panel, a rear deck panel, or the like. Such panels have relatively complex shape and outer panels, at least, must retain a commercially acceptable outer surface for painting.

In general, the sheet metal starting material is prepared from a suitable cast ingot or slab of a desired magnesium-base alloy. A magnesium alloy that is widely available in sheet metal forming is the alloy designated AZ31B. The nominal composition by weight of this alloy is about three percent aluminum, one percent zinc, limited amounts of impurities, and the balance magnesium. The homogenized ingot or slab is progressively subjected to one or more hot or warm rolling operations to reduce the cast metal to a strip and then to a sheet of suitable width, thickness, and surface quality. The hot or warm rolled material may be annealed between rolling stages. After several rolling stages a relatively long sheet of magnesium alloy material is obtained and it is rolled by the manufacturer into a coil. The coiled material is annealed to form a metallurgical microstructure in the coiled sheet that is desired for the intended use of the sheet material. In order to obtain suitable formability of the sheet material it has been considered prudent to start with a coil of magnesium alloy sheet material that has been fully annealed to an O-temper condition. It has been understood that a coiled roll of such O-temper magnesium sheet material would exhibit good formability and good surface quality in the formed product.

It has now been discovered that such coiled O-temper magnesium alloy sheet is vulnerable to small amounts of cold work from sheet processes like tension leveling, coiling/decoiling, and incidental hammering or striking of the sheet. This small amount of cold work, upon heating to warm forming or hot stretch forming temperatures, gives rise to large recrystallized grains typically near the sheet surface. It is found that these large grains lead to lower sheet metal ductility, lower formability, and orange-peel surface effects in formed parts. While the amount of cold work may be small, it has been introduced into soft O-temper material. The localized cold work may be tolerated in some magnesium sheet forming practices. But when automotive body panels and like articles of complex shape are formed at elevated temperatures the previously unexpected change in formability presents manufacturing problems.

In accordance with embodiments of this invention, a recovery heat treatment is provided for sheet metal blanks or workpieces removed from a coil of O-temper magnesium alloy intended for hot forming such as warm stamping or Quick Plastic Forming, a form of hot blow forming in which the air pressure is increased during forming in accordance with a pressure schedule. For example, the recovery heat treatment may be applied to a blank or group of blanks unwound and cut from the same O-temper coil of a magnesium alloy such as AZ31B.

The blanks are heated to a predetermined temperature that is frequently in the range of about 200° C. to about 350° C. The heat treatment temperature for a specific alloy and workpieces of blank material is determined by experience or by experiment as described below in this specification. The duration of the heat treatment is also predetermined and is often for a period of minutes up to about sixty minutes. The purpose of the recovery heat treatment is to repair the effect of the incidental and often unavoidable cold work in the magnesium alloy sheet material without unduly increasing its grain size. The goal is to commence hot stamping or hot blow forming of magnesium alloy sheet material that has been returned to a uniformly ductile and formable state for the stretch forming of the blank into a well formed sheet metal product with commercially acceptable surface quality.

Other objects and advantages of the invention will become apparent from a description of specific illustrative examples.

BRIEF DESCRIPTION OF THE DRAWINGS

The FIGURE is a bar graph illustrating forming data in terms of Terminal Dome Height in millimeters obtained from test recovery heat treatments on representative blanks obtained from a cold rolled coil of AZ31B magnesium alloy annealed to an O-temper condition. The magnesium alloy blanks were formed by a bulge test into hemispherical dome shapes after indicated recovery heat treatment temperatures and times. In general, a greater value of Terminal Dome Height indicates a recovery heat treatment (heat treatment temperature and time) that provides better formability in the magnesium alloy sheet material.

DESCRIPTION OF PREFERRED EMBODIMENTS

Traditionally, hot metal forming processes for magnesium alloys involves acquiring one or more coils of a selected magnesium alloy in the O-temper condition. Flat blanks of sheet metal are obtained from the coils for the manufacture of formed sheet metal parts such as automotive body panels. A blank of suitable thickness and plan view shape of the acquired O-temper sheet metal workpiece is heated to some elevated temperature, held at that temperature for a short time, and then deformed at that temperature to form a useful shape. The process is repeated many times in the manufacture of articles of manufacture like panels for vehicle doors, deck lids, tail gates, hoods, and the like.

This invention has been demonstrated to be beneficial for hot blow forming of sheets of AZ31B magnesium alloy which is a commercially available and commonly used magnesium alloy sheet. AZ31B material is available in O-temper. The O-temper sheet material has a fully annealed microstructure characterized by a varied grain size with a somewhat bimodal distribution of grain sizes. Typically the grain sizes are in a range of about 5-20 micrometers. The invention will also be beneficial for other hot forming processes, other starting shapes, and other magnesium alloys.

It is found that the coiling and handling of O-temper magnesium alloy sheet material introduces a small amount of cold work into the microstructure of the annealed material. The cold work typically comes from converting the annealed, coiled sheet to a flat sheet preparatory to preparing metal blanks for placing in a press for hot forming. It takes more work to flatten the material on the inner diameter of the coil than on the outer diameter of the coil. Thus, there can be a variation in the amount of work introduced into the sheet as the coil is unwound. Such cold work is commonly found in the surface of the un-coiled material from which sheet metal blanks are cut for hot forming processes. This small amount of cold work, which is non-uniform and inconsistent in the coil, leads to microstructural changes which give lower formability than the nominal temper would suggest.

Practices of the invention may depend in part on the quantity of coils of a particular specified O-temper magnesium alloy that are used in a manufacturing line or plant. For example, in a large volume manufacturing situation it may be desired to eliminate an inconsistent level of cold work from coil to coil, and potentially from supplier to supplier. One may be willing to develop a recovery heat treatment for each coil or each supplier, or one may choose to develop a single heat treatment that may be applied to all the blanks from a given supplier or all suppliers. In the latter case, such a method could be to evaluate multiple coils of material and select sheet metal samples representing extremes in cold work pre-strains which could be present. Material would be sampled from the ends and middle of the coils. In this example, the following test procedure could be practiced to determine the time-temperature parameters of a recovery heat treatment required to eliminate the strain in all such samples with out deleterious effects of recrystallization on the intended following hot forming operations. Such recovery heat treatment would likely then be applied to a stack of leveled and sheared blanks preparatory to lubrication and forming. As an alternative the blanks may be heat treated as a pert of a process for lubricating the blanks.

In accordance with this invention representative samples of the candidate magnesium alloy O-temper material for forming are tested to determine whether they require a recovery heat treatment before hot forming.

Such testing may, for example, comprise unconstrained hot blow forming of AZ31B-O sheet specimens into hemispherical domes at an intended hot forming temperature of about 350° C. to about 500° C. The lower temperatures may be applicable to evaluate magnesium alloy blanks for hot stamping and the higher temperatures to evaluate blanks for hot blow forming.

In one embodiment of this testing, a square magnesium alloy blank (175 mm on a side) at room temperature is placed in a die which is maintained at a forming temperature such as 450° C. One face of the sheet is placed to overlie a circular 100 mm diameter opening in a die plate and the sheet is heated by the hot die. When the sheet reaches a selected temperature for formability evaluation, gas pressure is applied to the other side of the sheet to expand the sheet through the hole into an unconstrained dome shape (a generally hemispherical shape). The gas pressure may be increased in stages or applied at a predetermined pressure level. After the sheet has reached a finished dome height or has torn, the bulge test is stopped and the formed specimen evaluated. The finished dome height, or Terminal Dome Height, in millimeters is a measure of the formability of the magnesium alloy blank at the forming test temperature.

In the following series of tests some of the O-temper magnesium alloy blanks were subjected as obtained from coiled material to the dome test and some were first subjected to a range of recovery heat treatments before the specimens were reheated and subjected to the dome-forming bulge tests. In other words, the blanks were subjected to varying heat treatments to determine a best recovery heat treatment for the particular magnesium alloy material represented by the small blanks.

In a first example the dome bulge test was performed on an AZ31B-O blank which had first been heat treated at 200° C. for fifteen minutes and cooled to room temperature. The forming of the dome was then conducted at 450° C. with an air pressure of 75 psi. The height of the dome reached a maximum of about 55 mm as summarized in the labeled (200 C 15 min) bar graph of the drawing figure. In this series of tests five other domes were formed using other blanks of the AZ31B-O sheet material that had been subjected to other recovery heat treatment schedules. The dome heights in millimeters of the respective bulge tests are provided as bar graphs in the drawing figure. It is seen that the as-received (no heat treatment) sample formed to a dome height of only about 50 mm. In this illustrative series of tests, recovery heat treatment temperatures ranged from 150° C. to 350° C. and heat treatment times ranged from 15 minutes to one hour. In these tests on these O-temper AZ31B materials, the largest dome height of almost 58 mm was attained after the O-temper material was heated at 200° C. for 30 minutes.

Thus, in the practice of the invention, a coil of O-temper magnesium alloy sheet material is evaluated before blanks of the material are committed in hot stamping or hot blow forming operations to make sheet metal parts of complex shape such as body panels for automotive vehicles. The above described dome bulge test or other suitable formability test may be used in evaluation of a new coil of O-temper magnesium alloy. A series of candidate recovery heat treatments based on a devised pattern of temperatures and heating times may be tried on small blanks of the material and the formability of the test blanks evaluated. A pattern of temperatures and heating times may be based on previous experience with coiled magnesium alloys or may be based on a selected starting treatment with variations until improvements in formability are realized. After a preferred heat treatment for the specific coil or coils is determined, it may be evaluated in heat treating the full size blanks used for production parts. Of course experience with the practice of the invention will improve the correlation of the recovery heat treatments performed on test banks with the formability of full size parts.

This practice of identifying and using a recovery heat treatment on initially coiled O-temper magnesium alloy sheet material improves the ductility and formability of the sheet material and yields hot formed parts with better surface quality in formed surfaces of the part.

Practices of the invention have been shown by examples that are presented as illustrations and not limitations of the invention.

The invention claimed is:

1. A method of improving the formability in a predetermined hot forming process of sheet material obtained from one or more coils of initially O-temper magnesium alloy sheet which has experienced cold work in obtaining forming blanks from the coiled material; the method comprising:
    subjecting test sheet specimens from the coiled sheet material to candidate heat treatments, the heat treatments comprising heating specimens at candidate temperatures in the range of about 200° C. to 350° C. for periods of about one minute to sixty minutes;
    conducting forming tests on respective heat treated specimens to provide formability test results; and
    using the formability test results to selectively determine a heat treatment schedule of time and temperature for subsequent stamping or forming of sheet metal blanks removed from the coil for forming sheet metal.

2. A method of improving the formability of coiled magnesium alloy sheet material as recited in claim 1 wherein conducting forming test comprises hot forming hemispherical domes from the heat treated specimens and determining the height and surface quality of the formed domes.

3. A method of improving the formability of coiled magnesium alloy sheet material as recited in claim 1 wherein conducting forming test comprises specimens is assessed by hot blow forming hemispherical domes from the heat treated specimens and determining the height and surface quality of the formed domes.

4. A method of improving the formability of coiled magnesium alloy sheet material as recited in claim 1 wherein conducting forming test comprises hot blow forming hemispherical domes from the heat treated specimens at the intended hot forming temperature and determining the height and surface quality of the formed domes.

5. A method of improving the formability of coiled magnesium alloy sheet material as recited in claim 1 in which the determined heat treatment schedule is used, at least initially, in the heat treatment of production size workpieces for the forming of production size parts by the predetermined hot forming process.

6. A method of improving the formability in hot stamping or hot blow forming of sheet material obtained from one or more coils of initially O-temper magnesium alloy sheet which has experienced cold work due to coiling, un-coiling, leveling, or handling of the coiled material; the method comprising:
    subjecting test sheet specimens from the coiled sheet material to candidate heat treatments, the heat treatments comprising heating specimens at candidate temperatures in the range of about 200° C. to 350° C. for periods of about one minute to sixty minutes;
    conducting forming tests on respective heat treated specimens to provide formability test results;
    using the forming test results to selectively determine a heat treatment schedule of time and temperature for subsequent stamping or forming of sheet metal blanks removed from the coil for forming sheet metal products by hot stamping or hot blow forming.

7. A method of improving the formability of coiled magnesium alloy sheet material as recited in claim 6 wherein conducting forming test comprises hot forming hemispherical domes from the heat treated specimens and determining the height and surface quality of the formed domes.

8. A method of improving the formability of coiled magnesium alloy sheet material as recited in claim 6 wherein conducting forming test comprises hot blow forming hemispherical domes from the heat treated specimens and determining the height and surface quality of the formed domes.

9. A method of improving the formability of coiled magnesium alloy sheet material as recited in claim 6 wherein conducting forming test comprises hot blow forming hemispherical domes from the heat treated specimens at the intended hot stamping or hot blow forming temperature and determining the height and surface quality of the formed domes.

10. A method of improving the formability of coiled magnesium alloy sheet material as recited in claim 6 in which the determined heat treatment schedule is used, at least initially, in the heat treatment of production size workpieces for the forming of production size parts by the predetermined hot forming process.

11. A method as set forth in claim 1 further comprising subjecting other portions of the coil sheet to the selectively determined heat treatment schedule of temperature and time and thereafter subjecting the heat treated other portions of the coil sheet to forming or stamping processes to provide a shaped sheet metal part.

12. A method as set forth in claim 6 further comprising subjecting other portions of the coil sheet to the selectively determined heat treatment schedule of temperature and time and thereafter subjecting the heat treated other portions of the coil sheet to forming or stamping processes to provide a shaped sheet metal part.

* * * * *